United States Patent
Alonso

(10) Patent No.: US 8,227,749 B2
(45) Date of Patent: Jul. 24, 2012

(54) PULSED FLOW ION MOBILITY SPECTROMETER

(75) Inventor: David Ruiz Alonso, Cambridge (GB)

(73) Assignee: Owlstone Limited, Cambridge, Cambridgeshire (GB)

( * ) Notice: Subject to any disclaimer, the term of this patent is extended or adjusted under 35 U.S.C. 154(b) by 567 days.

(21) Appl. No.: 12/305,613

(22) PCT Filed: Jun. 19, 2007

(86) PCT No.: PCT/GB2007/050342
§ 371 (c)(1),
(2), (4) Date: Aug. 7, 2009

(87) PCT Pub. No.: WO2007/148131
PCT Pub. Date: Dec. 27, 2007

(65) Prior Publication Data
US 2011/0198490 A1    Aug. 18, 2011

(30) Foreign Application Priority Data

Jun. 19, 2006 (GB) .................... 0612042.2

(51) Int. Cl.
*H01J 49/34* (2006.01)
(52) U.S. Cl. ........................................................ 250/286
(58) Field of Classification Search .................. 250/286, 250/287, 281, 282
See application file for complete search history.

(56) References Cited

U.S. PATENT DOCUMENTS

| | | | |
|---|---|---|---|
| 4,777,363 A * | 10/1988 | Eiceman et al. | 250/286 |
| 7,511,268 B2 * | 3/2009 | Landgraf | 250/288 |
| 7,579,589 B2 * | 8/2009 | Miller et al. | 250/292 |
| 2004/0164238 A1 | 8/2004 | Xu et al. | |
| 2004/0240843 A1 | 12/2004 | Miller et al. | |
| 2005/0133716 A1 | 6/2005 | Miller et al. | |

* cited by examiner

*Primary Examiner* — Kiet T Nguyen
(74) *Attorney, Agent, or Firm* — Edwards Wildman Palmer LLP; Barry Kramer

(57) ABSTRACT

An ion mobility spectrometer is described which makes use of a pulsed flow pump to draw gas through an ion filter in pulsed operation. A gas counterflow may also be provided, in some embodiments this may also be a pulsed counterflow.

25 Claims, 2 Drawing Sheets

PULSED FLOW ION MOBILITY SPECTROMETER

FIELD OF THE INVENTION

The present invention relates to an ion mobility spectrometer, and more particularly to a field asymmetric ion mobility (FAIM) spectrometer, which is operated using a pulsed flow of gas. Aspects of the invention also relate to methods of performing ion mobility spectrometry using a pulsed flow of gas.

BACKGROUND TO THE INVENTION

Ion mobility spectrometry is a versatile technique used to detect presence of molecular species in a gas sample. The technique has particular application in detection of explosives, drugs, and chemical agents in a sample, although it is not limited to these applications. Portable detectors are commonly used for security screening, and in the defence industry. However, conventional portable devices are still nonetheless relatively large.

Ion mobility spectrometry relies on the movement of different ion species through an electric field to a detector; by appropriate selection of the parameters of the electric field, ions having differing properties will reach the detector at differing times, if at all. Time of flight (TOF) ion mobility spectrometry measures the time taken by ions when subject to an electric field to travel along a drift tube to a detector. Ions of different characteristics will reach the detector at different times, and the composition of a sample can be analysed. This form of spectrometry relies on the length of the drift tube for its resolution; the longer the drift tube, the more powerful the detector. This restricts the possible miniaturisation of such spectrometers, since there is a limit to the lower size of the drift tube which may effectively be used. Further, given that relatively high electric field strengths are necessary, the restriction on drift tube length also results in the need to use relatively high voltages in the device, which may be potentially hazardous to the operator and further restricts the possibility of miniaturisation of the device.

A variation on TOF ion mobility spectrometry is described in U.S. Pat. No. 5,789,745, which makes use of a moving electrical potential to move ions against a constant drift gas flow towards a detector. A plurality of spaced electrodes are alternately pulsed to generate a moving potential well, which carries selected ions along with it. This device is unsuited to miniaturisation due to, among other reasons, the need for a pump to produce the drift gas flow.

Field asymmetric ion mobility spectrometry (FAIMS) is a derivative of time of flight ion mobility spectrometry (TOFIMS), which potentially offers a smaller form factor; however, existing designs use moving gas flows and high voltages, which are undesirable for microchip implementations. Scaling is further hindered by molecular diffusion, an effect that becomes significant in the micron regime. Background information relating to FAIMs can be found in L. A. Buryakov et al. Int. J. Mass. Spectrom. Ion Process. 128 (1993) 143; and E. V. Krylov et al. Intl. Mass. Spectrom. Ion Process. 225 (2003) 39-51; hereby incorporated by reference.

Conventional FAIMS operates by drawing air at atmospheric pressure into a reaction region where the constituents of the sample are ionized. Chemical agents in vapour-phase compounds form ion clusters. The mobility of the ion clusters is mainly a function of shape and weight. The ions are blown between two metal electrodes, one with a low-voltage DC bias and the other with a periodic high-voltage pulse waveform, to a detector plate where they collide and a current is registered. Ions are quickly driven toward one electrode during the pulse phase and slowly driven toward the opposite electrode between pulses. Some ions impact an electrode before reaching the detector plate; other ions with the appropriate differential mobility reach the end, making this device a sort of differential mobility ion filter. A plot of the current generated versus DC bias provides a characteristic differential ion mobility spectrum. The intensity of the peaks in the spectrum, which corresponds to the amount of charge, indicates the relative concentration of the agent.

While this arrangement offers the possibility for greater miniaturisation than conventional TOFIMS, the need to generate a constant gas flow requires the presence of a pump, which limits the lower size of such a device. Representative examples of such devices are described in U.S. Pat. Nos. 6,495,823 and 6,512,224.

We have developed a further modification of PAWLS, which is described in international patent publications WO 2006/046077 and WO 2006/013396. The content of these publications is incorporated herein by reference. As described in these publications, the technique does not require a drift gas flow for its operation. Instead, an electric field is used to cause ions to move toward the detector. An ion filter having a plurality of ion channels formed by an interdigitated array of electrodes is used; the electrodes are operated so as to produce both a filter and a drive electric field. The drive field serves to drive ions through the filter, in place of a drift gas flow, while the filter field acts to permit only selected ions through the filter. This arrangement allows for a solid state construction which does not require a gas pump or similar, so allowing for greater miniaturisation of the device than would otherwise be possible, as well as a more robust construction.

We have now devised a modification of these devices, in which a pulsed drift gas flow is used. The pulsed drift gas flow has benefits in terms of pre-concentrating ions to be detected, and may be used to improve sensitivity. Further, a fixed mass of analyte introduced into the spectrometer will not be diluted as with a continuous drift gas flow, so increasing sensitivity. Relatively small pumps may be used to generate a pulsed flow, so maintaining the advantages of miniaturisation offered by the ion filter arrangement described above. The pulsed flow arrangement may be used with alternative ion filter geometries, such as those used in conventional FAIMS.

SUMMARY OF THE INVENTION

According to a first aspect of the present invention, there is provided an ion mobility spectrometer comprising an ionizer, an ion detector, an ion filter defining at least one ion channel along which ions may pass from the ionizer to the ion detector, and a pump operable to draw gas through the ion filter in pulsed operation.

By 'pulsed operation' is meant that the pump operates in an intermittent or non-continuous manner; the pump may operate in an on-off cycle, or in a flow-counterflow cycle, or in a combination of the two. Preferably the pump draws gas from the ionizer through the filter and toward the detector; alternatively the pump may draw gas along only part of this route (for example, electric fields may be used to move ions over the remainder of the route). Alternatively the pump may draw gas in the reverse direction, from the detector through the filter toward the ionizer; or in both directions in a flow-counterflow cycle.

The ions generated by the ionizer are intermittently drawn through the filter; selected ions are able to pass through the filter and be detected by the ion detector. When the pump is not operating, ions are not drawn through the filter and are allowed to accumulate adjacent the filter. This increases the effective concentration of ions passing through the filter when the pump does operate, thereby improving sensitivity of the spectrometer. Another pre-concentration effect may be achieved over multiple cycles; for example, where the pump operates in a counterflow mode, ions will move through the filter to the detector when the pump is off; when the pump is operating, uncharged particles will be returned through the filter to be reionized and redetected in subsequent cycles. This recycling of ions increases the effective concentration of the analyte. A similar effect may be obtained by driving the ions by electrical fields against a lower counterflow generated by a pump; uncharged particles will be driven only by the counterflow and returned to the ionizer.

Further, a pump operable in pulsed operation may be reduced in size compared with a conventional continuous pump, thereby permitting miniaturisation of the spectrometer. Suitable pumps will be known to the skilled person; for example, the pump may be a diaphragm pump, speaker pump, piezoelectric pump, peristaltic pump, or the like.

The spectrometer may also comprise means for generating a first drive electric field to draw ions from the ionizer toward the ion filter. This generating means may comprise one or more electrodes arranged adjacent the ion filter; for example, the spectrometer may comprise a deflector electrode located adjacent the ionizer to direct ions away from the ionizer. The ion detector may comprise a second electrode coupled to the deflector electrode to attract ions.

The spectrometer may further comprise means for generating a second drive electric field to draw ions through the ion filter. This generating means may comprise one or more electrodes which are part of the ion filter. For example, the generating means may comprise means for controlling electrodes arranged adjacent the ion channel such that a drive electric field is generated along the length of the ion channel, and a second filter electric field is generated orthogonal to the drive field. Preferably also each of said electrodes is involved in generating a component of both the drive and filter electric fields. This is essentially the arrangement of the ion filter as described in WO 2006/013396.

The ion filter preferably comprises a plurality of electrodes; the filter preferably defines multiple ion channels. As an alternative to the ion filter arrangement described in our previous international patent applications, the ion filter may comprise at least one pair of electrodes disposed along the ion channel, such that the electrodes may be used to generate an electric field orthogonal to the direction of ion flow along the channel.

The spectrometer may further comprise a drift gas source; the drift gas is conveniently an inert gas such as neon or the like. Alternatively the drift gas used may be air; the spectrometer preferably comprises a scrubber for cleaning the drift gas. The scrubber may include a filter for removing particulates from the gas; and/or a dehumidifier for controlling the moisture content of the gas. The scrubber may comprise a porous material; for example a porous ceramic, or expanded PTFE or the like. The scrubber may comprise activated carbon or similar, to remove for example organic volatiles from the drift gas. A scrubber may also be present even when no drift gas source is used; in this case the spectrometer will use atmospheric air as a drift gas which will be cleaned by the scrubber.

The spectrometer may comprise means for generating a gas counterflow; that is, a flow of gas in the opposite direction from that of the pump. Typically the pump will operate to draw ions through the filter from the ionizer side to the detector side;

the counterflow will then be operable to draw gas from the filter toward the ionizer. In preferred embodiments, the same pump is operable to provide a pulsed gas flow and a counterflow; in these embodiments the counterflow will operate alternately with the flow. In certain embodiments, however, a counterflow may be generated by a separate pump, and may operate simultaneously with the flow. Generation of a counterflow will serve to deflect non-charged particles away from the filter; where the counterflow alternates with the flow, non-charged particles may be returned to the ionizer and subjected to further ionisation and an additional detection step. In this way the sensitivity of the spectrometer will be increased, as each particle of analyte is more likely to be detected. Further, where the spectrometer comprises a deflector electrode, this may be operated at the same time as the counterflow is generated; ions will thereby be retained within the spectrometer while non-ionised particles may be ejected by the counterflow.

The counterflow may be continuous, but is preferably pulsed. The flow and counterflow are preferably asymmetric; that is, either the time or the magnitude or both of the flow and counterflow are unequal. Preferably the overall volume of gas passed during the flow and counterflow are equal. In a preferred embodiment, the counterflow is of lesser magnitude but greater duration than the flow.

Preferably the means for generating a counterflow is also operable to purge the spectrometer prior to a measurement cycle of the spectrometer. For example, a counterflow may be generated prior to initial operation of the spectrometer in order to purge any ions from the spectrometer. Where the spectrometer comprises a deflector electrode, this may be deactivated during the purge cycle to allow ions to leave the spectrometer.

Preferably the spectrometer further comprises means for synchronising the operation of the ion detector with the operation of the flow pump. In its simplest form, this may comprise activating the ion detector only when the flow pump is activated; when there is no gas flow, the ion detector need not be activated since little or no useful data will be obtained. The spectrometer may further comprise means for combining a plurality of ion detection operations into a single measurement.

According to a further aspect of the present invention, there is provided a method of operating an ion spectrometer, the method comprising operating a pump in pulsed operation to non-continuously draw ions through an ion filter.

The method may further comprise operating a pump to generate a counterflow to draw ions from the ion filter toward the ionizer. The counterflow may be continuous, but is preferably pulsed, and more preferably alternates with the flow. Preferably the flow and counterflow are asymmetric; that is, either the time or the magnitude or both of the flow and counterflow are unequal. Preferably the overall volume of gas passed during the flow and counterflow are equal. In a preferred embodiment, the counterflow is of lesser magnitude but greater duration than the flow.

The method may further comprise the step of generating a counterflow prior to initial operation of the spectrometer, to purge the interior of the spectrometer.

A still further aspect of the present invention provides an ion mobility spectrometer comprising an ionizer, an ion detector, an ion filter defining at least one ion channel along which ions may pass from the ionizer to the ion detector, means for generating an ion flow from the ionizer toward the ion filter, and a pump for generating a non-continuous counterflow from the ion filter toward the ionizer.

This aspect of the invention provides for a pulsed counterflow in combination with a flow. The means for generating an ion flow may be operable in a non-continuous manner, or may be operable continuously. The ion flow means may comprise a pump, or may comprise means for generating a drive electric field.

A yet further aspect of the present invention provides an ion mobility spectrometer comprising an ionizer, an ion detector, an ion filter defining at least one ion channel along which ions may pass from the ionizer to the ion detector, and flow generator means operable to generate an ion flow through the ion filter in pulsed operation. In this aspect of the invention, the flow generator means is preferably a pump as previously described, but may instead or in addition comprise means for generating a drive electric field. While pulsed operation of an electric field is not as advantageous as a pulsed pump, there may nevertheless still be some benefit in terms of pre-concentration of ions, improved sensitivity, and the like.

BRIEF DESCRIPTION OF THE DRAWINGS

These and other aspects of the present invention will now be described, by way of example only and without limitation, with reference to the accompanying figures in which.

DETAILED DESCRIPTION OF THE DRAWINGS

Figure 1:
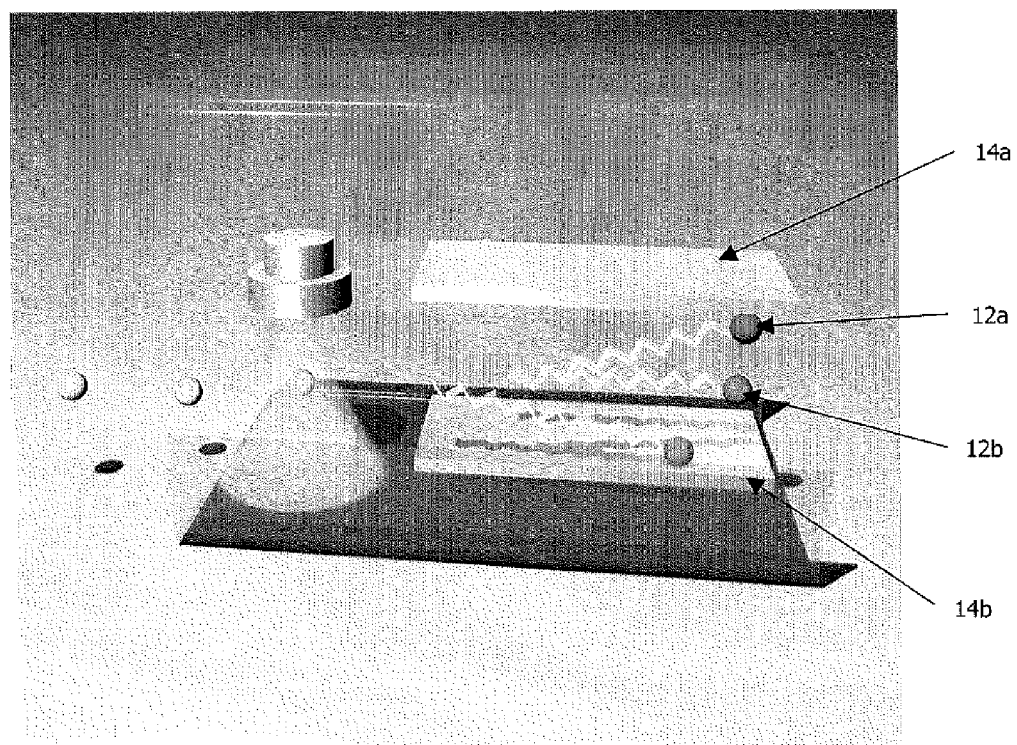
FIG. 1 shows in schematic form the conventional operation of a FAIMS device.

FIG. 1 shows in a schematic form the operation of conventional FAIMS (field asymmetric ion mobility spectroscopy). Air is drawn at atmospheric pressure into a reaction region where the constituents of the sample are ionized. The ions 12a, 12b are blown between two metal electrodes 14a, 14b, one with a low-voltage DC bias and the other with a periodic high-voltage pulse waveform, to a detector plate (not shown) where they collide and a current is registered. Ions are quickly driven toward one electrode during the pulse phase and slowly driven toward the opposite electrode between pulses. Some ions 12a impact an electrode before reaching the detector plate; other ions 12b with the appropriate differential mobility reach the end, making this a differential mobility ion filter. A plot of the current generated versus DC bias provides a characteristic differential ion mobility spectrum. The intensity of the peaks in the spectrum, which corresponds to the amount of charge, indicates the relative concentration of the agent. Importantly, note that air is drawn only in a single direction, and is pumped continuously. To provide such a continuous flow through the device, air must be pumped at a rate on the order of 1 l/min to 10 l/min. In order to achieve this a continuous flow pump is needed which is typically relatively large, costly, and high in power consumption.

Figure 2:
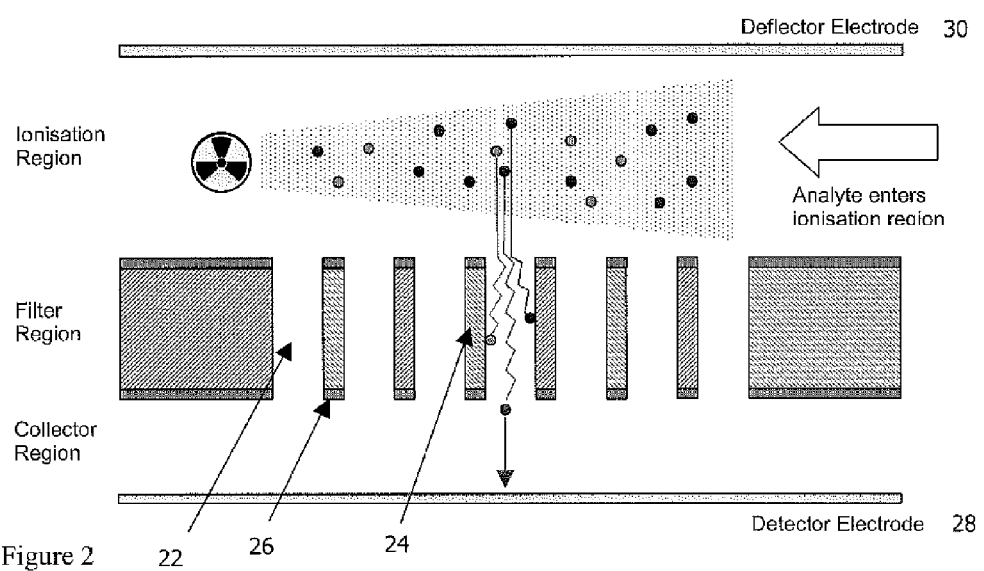
FIG. 2 shows the operation of a FAIMS device using an ion filter arrangement as described in WO 2006/013396.

An improved FAIMS device and ion filter is described in international patent publication WO 2006/013396; as described this device does not make use of a gas flow, but instead generates ion flow by virtue of a drive electric field created by the filter electrodes. A schematic diagram of the operation of this filter is shown in FIG. 2. An interdigitated electrode structure is formed by etching a dense array of narrow channels through high resistivity silicon. Ions are driven through the channels via a transport mechanism relying on electric fields instead of moving gas flows to achieve pumpless operation. Ion channels 22 are defined by the silicon substrate 24 which carries a conductive layer 26, defining electrodes at each corner of the entrance to and exit from the ion channel. Note that the metal plates are replaced by high resistivity silicon. The detector electrode 28 in this embodiment is disposed orthogonal to the ion channels 22. In addition to a high-voltage pulse and low voltage DC bias generated across the channel, a further DC source is applied to a deflector electrode 30 to create a drive electric field to drive ions through the channel, eliminating the need for a moving gas flow. The filter is typically operated with an electric field of 40 to 200 V across the channel, with the high-voltage pulse being typically from 3 MHz to 10 or 20 MHz. The drive field may generally be from 10 to 40 V. As described, this filter arrangement does not require any gas flow for its operation, so permitting high levels of miniaturisation, and reduction in power consumption.

However, we have determined that in some circumstances it can be desirable to use a gas flow pump through the device; and in particular a pulsed operation gas flow.

Figure 3:
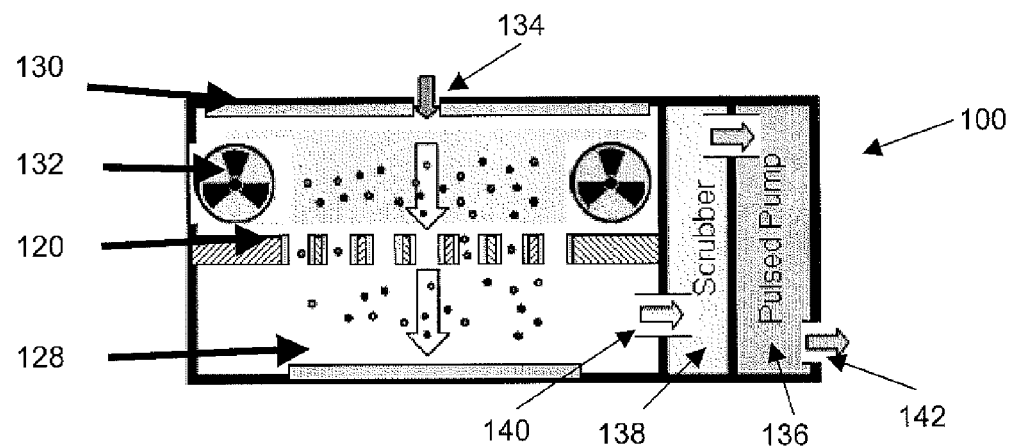
FIG. 3 shows an embodiment of an ion spectrometer in accordance with a first aspect of the present invention, being operated with a gas flow in a first direction.

FIG. 3 shows an ion spectrometer designed for operation with a pulsed gas flow, being a modified version of the spectrometer shown in FIG. 2. The spectrometer 100 includes an ion filter 120 of the type shown in FIG. 2, having a plurality of ion channels formed by a silicon substrate having electrodes located at the outer surfaces of the channels. The filter 120 is located between an ion deflector electrode 130 and an ion detector electrode 128. The deflector electrode 130 includes an opening 134 which allows access to the interior of the spectrometer. A radiation source 132 is located between the deflector electrode 130 and the ion filter 120, to create an ionization region.

The spectrometer also includes a pump 136 operable in a pulsed mode which is in communication with the interior of the spectrometer via a scrubber 138 and air flow opening 140; this opening is in the portion of the spectrometer adjacent the ion filter 120 and the detector electrode 128. The pulsed pump 136 is also in communication with the atmosphere via a further air flow opening 142.

The spectrometer is operated as follows. The first cycle is a measurement cycle, and is depicted in FIG. 3. Ions are driven by the deflector electrode 130 from the ionization region 132 toward the ion filter 120. The pulsed pump 136 is operated to draw air and ions through the filter 120; this also serves to draw new air to be sampled into the ionization region 132 via the opening 134. The new sample is ionized in the ionization region, and the sample is drawn through the ion filter 120 by the flow of air in combination with the operation of the deflector electrode 130.

The ion filter 120 operates to allow selected ions to pass through the filter; uncharged particles will also pass through the filter. Ions will collide with the detector electrode 128 and be detected by the spectrometer. As the pump operates, air is drawn from the spectrometer through the scrubber 138, which prevents contaminants being vented into the atmosphere, and scrubbed air may be expelled to atmosphere via opening 142.

Figure 4:
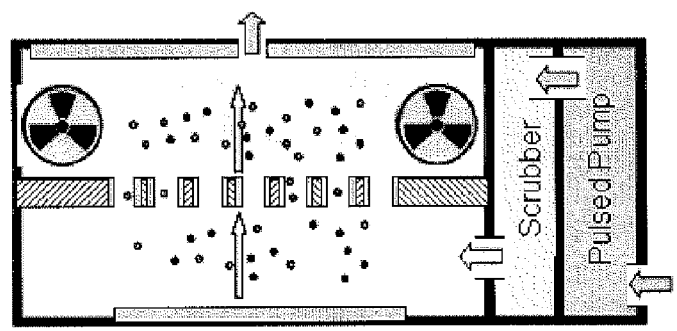
FIG. 4 shows the spectrometer of FIG. 3, being operated with a gas counterflow.

The second cycle of operation is a recovery cycle, and is depicted in FIG. 4. The operation of the pulsed pump 136 is reversed, such that air is drawn into the pump from the opening 142, and passed through the scrubber 138 into the interior of the spectrometer. The pulsed pump 136 is operated at a lower flow rate than in the measurement cycle. Although the flow rate is lower, the overall volume of air moved in the recovery cycle may be greater than, equal to, or less than, that moved in the measurement cycle. The scrubber 138 ensures that contaminants do not enter the spectrometer from the atmosphere, and further serves to regulate moisture content of the air within the spectrometer; this is important to obtain consistent results from the spectrometer.

Air is thus driven from the ion detector side of the spectrometer through the ion filter 120 into the ionization region 132. The ion filter is typically deactivated for this cycle, and any uncharged particles which are in the detector side of the spectrometer will be returned to the ionization region. As the pump continues to operate, uncharged particles will either become ionized as they dwell in the ionization region, or will be expelled from the spectrometer through opening 134. Operation of the deflector electrode 130 serves to retain ions within the spectrometer. This process increases the concentration of ions within the spectrometer, so serving as a pre-concentration step prior to the next measurement cycle. Further, the recycling of ions and uncharged particles during the recovery cycle is an additional means of improving sensitivity of the spectrometer.

Modifications of this basic operation are possible. For example, it is not essential to use a recovery cycle; a simple pulsed unidirectional flow would provide at least some of the advantages of the present invention, such as a pre-concentration step. An initial purging of the spectrometer could also be provided by operating the spectrometer as for the recovery cycle, but with the deflector electrode deactivated to allow ions and uncharged particles within the spectrometer to be expelled prior to the first measurement cycle.

In embodiments in which an electric field is also used to drive ions through the filter, it is preferred that this field is not applied during the recovery cycle, to allow ions to pass back through the filter.

Although continuous detection may be used, it may be desirable to deactivate the ion detector during the recovery cycle, to conserve energy. Further, successive measurements made during measurement cycles may be combined to give a single reading over time.

The relative flows during the measurement and recovery cycle may vary, depending on the characteristics of the sample to be detected; it is preferred that asymmetric flows are used, with the measurement flow being greater in magnitude and lesser in time than the recovery flow.

Although the spectrometer in FIGS. 3 and 4 has been shown as incorporating the ion filter structure of FIG. 2, it will be apparent that it is possible to use other filter geometries, such as that shown in FIG. 1 whereby the ion filter is defined by parallel plate electrodes. Multiple parallel electrodes may be used to define a plurality of ion channels, if desired. It is also possible in any of these embodiments to provide the device without the deflector electrode, and rely solely on gas flow to drive ion flow.

It will be seen that the present invention provides a number of advantages over conventional FAIMS. With a pulsed flow approach constraints on the size and type pump are relaxed since no continued high flow is required; this allows for smaller integrated pumps. Therefore other pump types are possible, such that we can build pressure over a relatively long time and release in a short time, creating a high flow pulse.

With a continued flow the analyte of interest will get diluted with the high flows, and relatively large masses of analyte are required. With the pulsed flow approach pre-concentration is achieved by analyte build up. Analyte is not wasted and is re-ionized and redetected. This way smaller masses of analyte can be detected. It is also possible to configure the device so that ionized analyte does not leave the analysis chamber by exhausting air from the chamber against an electric field generated by the deflector electrode near the ionization region. It is easier to make the device robust against humidity variation (and other changes in atmospheric air) since sampling does not need to be continuous and analyte can build up not having to compromise sensitivity.

The invention claimed is:

1. An ion mobility spectrometer comprising:
   a) an ionizer;
   b) an ion detector;
   c) an ion filter defining at least one ion channel along which ions may pass from the ionizer to the ion detector;
   d) a pump operable to draw gas through the ion filter in pulsed operation and;
   e) means for generating a drive electric field having one or more electrodes to draw ions through the ion filter, wherein said means for generating also forms at least a portion of the ion filter adapted and configured for controlling electrodes arranged adjacent the ion channel such that a first drive electric field is generated along the length of the ion channel, and a second filter electric field is generated orthogonal to the first.

2. The spectrometer of claim 1, wherein the pump is operable to draw gas from the ionizer toward the ion filter.

3. The spectrometer of claim 1, wherein the pump is operable to draw gas from the ion filter toward the ion detector.

4. The spectrometer of claim 1, wherein the pump is selected from the group comprising diaphragm pumps, speaker pumps, piezoelectric pumps, and peristaltic pumps.

5. The spectrometer of claim 1, further comprising means for generating a first drive electric field to draw ions from the ionizer toward the ion filter.

6. The spectrometer of claim 5, wherein the generating means comprises one or more electrodes arranged adjacent the ion filter.

7. The spectrometer of claim 5, wherein the generating means comprises a deflector electrode located adjacent the ionizer to direct ions away from the ionizer.

8. The spectrometer of claim 7, wherein the ion detector comprises a second electrode coupled to the deflector electrode to attract ions.

9. The spectrometer of claim 1, wherein each of said electrodes is involved in generating a component of both the drive and filter electric fields.

10. The spectrometer of claim 1, wherein the ion filter comprises a plurality of electrodes.

11. The spectrometer of claim 1, wherein the filter defines multiple ion channels.

12. The spectrometer of claim 1, wherein the ion filter comprises at least one pair of electrodes disposed along the ion channel, such that the electrodes may be used to generate an electric field orthogonal to the direction of ion flow along the channel.

13. The spectrometer of claim 1, further comprising a drift gas source.

14. The spectrometer of claim 1, further comprising a scrubber for cleaning the gas.

15. The spectrometer of claim 14, wherein the scrubber comprises a filter for removing particulates from the gas.

16. The spectrometer of claim 14, wherein the scrubber comprises a dehumidifier for controlling the moisture content of the gas.

17. The spectrometer of claim 1, further comprising means for generating a gas counterflow.

18. The spectrometer of claim 17, wherein the means for generating a counterflow is the pump operable to draw gas from the ionizer toward the ion filter in pulsed operation.

19. The spectrometer of claim 17, wherein the means for generating a counterflow is a separate pump.

20. The spectrometer of claim 17, wherein the counterflow is pulsed.

21. The spectrometer of claim 17, wherein the flow and counterflow are asymmetric.

22. The spectrometer of claim 17, wherein the overall volume of gas passed during the flow and counterflow are equal.

23. The spectrometer of claim 17, wherein the means for generating a counterflow is operable to purge the spectrometer prior to a measurement cycle of the spectrometer.

24. The spectrometer of claim 1, further comprising means for synchronizing the operation of the ion detector with the operation of the flow pump.

25. The spectrometer of claim 1, further comprising means for combining a plurality of ion detection operations into a single measurement.

* * * * *